US010895665B2

(12) United States Patent
Dhont et al.

(10) Patent No.: US 10,895,665 B2
(45) Date of Patent: Jan. 19, 2021

(54) METHOD FOR DETECTING HYDROCARBON DEPOSITS

(71) Applicant: Total SA, Courbevoie (FR)

(72) Inventors: Damien Dhont, Pau (FR); Dominique Dubucq, Pau (FR); Jean-Paul Xavier, Pau (FR); Sébastien Guillon, Pau (FR); Emmanuel Pajot, Pau (FR); Véronique Miegebielle, Pau (FR)

(73) Assignee: TOTAL SA, Courbevoie (FR)

( * ) Notice: Subject to any disclaimer, the term of this patent is extended or adjusted under 35 U.S.C. 154(b) by 0 days.

(21) Appl. No.: 15/503,339

(22) PCT Filed: Aug. 12, 2014

(86) PCT No.: PCT/FR2014/052082
§ 371 (c)(1),
(2) Date: Feb. 10, 2017

(87) PCT Pub. No.: WO2016/024050
PCT Pub. Date: Feb. 18, 2016

(65) Prior Publication Data
US 2017/0235015 A1    Aug. 17, 2017

(51) Int. Cl.
*G01N 33/24*    (2006.01)
*G06T 7/143*    (2017.01)
(Continued)

(52) U.S. Cl.
CPC .............. *G01V 9/007* (2013.01); *G01C 11/06* (2013.01); *G01N 33/241* (2013.01); *G01S 13/90* (2013.01);
(Continued)

(58) Field of Classification Search
CPC .. G01N 33/1833; G01N 33/24; G01N 33/241; G01N 33/2823; G01N 2021/1793;
(Continued)

(56) References Cited

U.S. PATENT DOCUMENTS 7,260,507 B2 *  8/2007  Kalayeh ............ G01N 21/3504
                                                  702/191
7,729,561 B1    6/2010  Boland et al.
(Continued)

FOREIGN PATENT DOCUMENTS

EP    1 279 970 A2    1/2003

OTHER PUBLICATIONS

Leifer et al., State of the art satellite and airborne marine oil spill remote sensing: Application to the BP Deepwater Horizon oil spill, Sep. 2012[retrieved Jun. 5, 2018], Remote Sensing of Environment, vol. 123, pp. 185-209. Retrieved from the Internet:https://www.sciencedirect.com/science/article/pii/S0034425712001563.*
(Continued)

*Primary Examiner* — Matthew C Bella
*Assistant Examiner* — Dennis Rosario
(74) *Attorney, Agent, or Firm* — Patterson Thuente Pedersen, P.A.

(57) ABSTRACT

The invention relates to a method for detecting and locating hydrocarbon deposits under a body of water in several steps. First, images of a surface of the body of water taken at different times are acquired. Next, for each image, traces of hydrocarbon leaks are identified. Next, a detection map is generated. This map indicates probabilities of the presence of a hydrocarbon leak around the identified traces. The map is obtained by processing the image at least based on a criterion of distance to the identified traces. Finally, the detection maps are combined to produce a hydrocarbon leak location map.

10 Claims, 5 Drawing Sheets

(51) Int. Cl.

| | |
|---|---|
| *G01V 9/00* | (2006.01) |
| *G01C 11/06* | (2006.01) |
| *G01S 13/90* | (2006.01) |
| *G06K 9/00* | (2006.01) |
| *G06T 7/00* | (2017.01) |
| *G06T 11/60* | (2006.01) |
| *G01N 21/17* | (2006.01) |

(52) U.S. Cl.
CPC .......... *G06K 9/0063* (2013.01); *G06T 7/0004* (2013.01); *G06T 7/143* (2017.01); *G06T 11/60* (2013.01); *G01N 2021/1793* (2013.01); *G06T 2207/30108* (2013.01); *G06T 2207/30181* (2013.01)

(58) Field of Classification Search
CPC ........ G01V 11/00; G01V 1/30; G01V 1/3808; G01V 1/38; G01V 9/007; G01V 1/003; G01V 1/362; G01V 99/005; G01V 8/00; G01V 8/02; H04L 67/12; G06F 3/0488; G07C 5/008; H04N 21/41422; H04N 7/181; G01C 21/00; G06T 7/20; G06T 2207/10032; G06T 2207/30192; G06T 7/143; G06T 7/0004; G06T 2207/30108; G06T 2207/30181; G06N 20/00; G06N 3/02; G06N 7/005; G06K 9/6263; G06K 9/0063; G06K 9/00697; G06K 9/00651; G06K 9/00771; G06K 9/629; G06K 9/00624; E21B 43/16; E21B 47/10
See application file for complete search history.

(56) References Cited

U.S. PATENT DOCUMENTS

| | | | | |
|---|---|---|---|---|
| 9,247,159 | B2* | 1/2016 | Brown | G01N 25/18 |
| 10,094,732 | B2* | 10/2018 | Linford | G01M 3/243 |
| 2010/0092241 | A1 | 4/2010 | Arshad | |
| 2011/0213554 | A1 | 9/2011 | Archibald | |
| 2018/0172544 | A1* | 6/2018 | MacMullin | G01F 1/00 |

OTHER PUBLICATIONS

Chaudhuri et al, A Statistical Approach for Automatic Detection of Ocean Disturbance Features From SAR Images, Aug. 2012[retrieved Jun. 5, 2018], IEEE Journal of Selected Tpoices in Applied Earth Observations and Remote Sensing, vol. 5, No. 4, pp. 1231-1242. Retrieved from the Internet: https://ieeexplore.ieee.org/stamp/stamp.jsp?tp=&arnumber=6210409.*

Li et al., Oil spill detection from SAR intensity imagery using a marked point process, Jul. 15, 2010 [retrieved Jun. 5, 2018], Remote Sensing of Environment, vol. 112, Issue 7,pp. 1590-1601. Retrieved from the Internet: https://www.sciencedirect.com/science/article/pii/S0034425710000817.*

Jha et al., Advances in Remote Sensing for Oil Spill Disaster Management: State-of-the-Art Sensors Technology for Oil Spill Surveillance, Jan. 21, 2008[retrieved Jun. 5, 2018], Sensors ,vol. 8, Issue 1, pp. 236-255. Retrieved from the Internet: http://www.mdpi.com/1424-8220/8/1/236/htm.*

Ferraro et al., Towards an operational use of space imagery for oil pollution monitoring in the Mediterranean basin: A demonstration in the Adriatic Sea, Apr. 2007[retrieved Jun. 5, 2018], Marine Pollution Bulletin, vol. 54, Issue 4,pp. 404-422. Retrieved from the Internet:https://www.sciencedirect.com/science/article/pii/S0025326X06005005.*

Gasull et al., Oil Spills Detection in SAR Images Using Mathematical Morphology, Sep. 3-6, 2002[retrieved Jun. 5, 2018], 2002 11th European Signal Processing Conference, 4 pages total. Retrieved from the Internet: https://ieeexplore.ieee.org/document/7071905/#full-text-section.*

Mukherjee et al., An Efficient Algorithm for Detection of Road-Like Structures in Satellite Images, Aug. 25-29, 1996[retrieved Jun. 5, 2018], 1996 Proceedings of the 13th International Conference on Pattern Recognition, pp. 875-879. Retrieved from the Internet:https://ieeexplore.ieee.org/abstract/document/547293/.*

Topouzelis, Oil Spill Detection by SAR Images: Dark Formation Detection, Feature Extraction and Classification Algorithms, Oct. 23, 2008 [retrieved Jun. 21, 2019], Sensors, vol. 8, No. 10,pp. 6642-6659. Retrieved: https://www.mdpi.com/1424-8220/8/10/6642 (Year: 2008).*

Alpers et al., SAR Marine User's Manual: Chapter 11. Oils and Surfactants, Jan. 2004 [retrieved Jun. 21, 2019], pp. cover+263-275. Retrieved: https://www.researchgate.net/publication/239531796_Chapter_11_Oils_and_Surfactants/download (Year: 2004).*

Sicot et al., Analysis of the reflectance spectra of oil emulsion spilled on the sea surface, Oct. 14, 2014 [retrieved Nov. 19. 2019], SPIE Remote Sensing of the Ocean, Sea Ice, Coastal Waters, and Large Water Regions, vol. 9240, 13 pages total. Retrieved: https://doi.org/10.1117/12.2067204 (Year: 2014).*

Leifer, Characteristics and scaling of bubble plumes from marine hydrocarbon seepage in the Coal Oil Point seep field, Nov. 19, 2010 [retrieved Nov. 19, 2019], Journal of Geophysical Research: Oceans: An AGU Journ, vol. 15, pp. 1-20. https://agupubs.onlinelibrary.wiley.com/doi/full/10.1029/2009JC005844 (Year: 2010).*

Hanna et al., Handbook on Atmospheric Diffusion, Jan. 1, 1982 [retrieved Sept. 19, 2020], Technical Information Center U.S. Department of Energy,110 ppages. Retrieved: https://www.osti.gov/biblio/5591108 (Year: 1982).*

PCT International Search Report for PCT/FR2014/052082, dated Apr. 16, 2015, 4 pages.

English translation of PCT International Search Report for PCT/FR2014/052082, dated Apr. 16, 2015, 3 pages.

PCT Written Opinion of the ISA for PCT/FR2014/052082, dated Apr. 16, 2015, 5 pages.

English translation of PCT Written Opinion of the ISA for PCT/FR2014/052082, dated Apr. 16, 2015, 6 pages.

N R G Cope et al: "OTC-25198-MS SS: Donation of Petrotechnical Data to Universities, Paper: Geohazards and Fluid Seepage Assessment on the Mad Dog Field Using Bathymetry, Ultra-high-resolution Seismic and Satellite Seepage Slick Data", May 8, 2014 (May 8, 2014), pp. 1-28. XP055181527, DOI: http://dx.doi.org/10.4043/25198-MS ISBN: 978-1-61-399308-8 Retrieved from the Internet: URL:https://www.onepetro.org/download/conference-paper/OTC-25198-MS!id=conference-paper/OTC-25198-MS [retrieved on Apr. 8, 2015].

"Identification of offshore natural seepages from SAR imagery" , D. Dhont, R.Lasnel, S. Riazanoff, D. Dubucq, S. Guillon, V Miegebielle, JP. Xavier, $34^{th}$ IGC—Brisbane / Aug. 2010, 16 pages, 1 page.

E. Pajot* , "Examples of SAR Imagery Applications to the Petroleum Industry" E. Pajot* (SPIE Oil and Gas Services), 75th EAGE Conference & Exhibition incorporating SPE Europec 2013 London, UK, Jun. 10-13, 2013, 5 pages.

Dhont et al., "Relationships Between Oil Seeps and Seabed Morphologies" , Paper No. 24242, Offshore Technology Conference 2013 May 6-9, 2013 , Houston , Texas, USA, 15 pages, 5 pages.

"Impact du mode de propagation de la déformation sur la préservation des sédiments dans les bassins intra-montagneux : Cas des Andes de Neuquén (Argentine)", Thème 2 Processus sédimentaire—$24^e$ Réunion des Sciences de la Terre—2.1.6 (o)—C. Bonnel, D. Huyghe, B. Niviére, G. Messager, D. Dhont, Y. Hervouët, JP. Xavier, B. Fasentieux, 1 page.

"Relationship between natural oil seeps and submarine morphology", Thème 2 Processus sédimentaire—$24^e$ Réunion des Sciences de la Terre—2.5.12 (o), R. Jatiault, D. Dhont, D. Dubucq, P. Imbert, L. Loncke, D. Levaché, V. Miegebielle, E. Cauquil, Thi Kim Lan Ho, 1 page.

I. R. MacDonald et al: "Natural oil slicks in the Gulf of Mexico visible from space", Journal of Geophysical Research, vol. 98, No. C9. Sep. 15, 1993 (Sep. 15, 1993), pp. 16351-16364, XP055181574, ISSN: 0148-0227, DOI: 10.1029/93JC01289.

Alpers et al. "Oils and Surfactants". Available at https://www.sarusersmanual.com/ManualPDF/NOAASARManual_CH11_pg263-276.pdf; Jan. 2004, 14 pgs.

(56) References Cited

OTHER PUBLICATIONS

Li et al. "Oil spill detection from SAR intensity imagery using a marked point process". Remote Sensing of Environment 114 (2010) 1590-1601.
MacDonald et al. "Natural Oil Slicks in the Gulf of Mexico Visible from Space". Journal of Geophysical Research, vol. 98, No. C9, Sep. 15, 1993, 15 pgs.
Topouzelis. "Oil Spill Detection by SAR Images:Dark Formation Detection Feature Extraction and Classification Algorithms". Sensors, 2008, 18 pgs.

* cited by examiner

METHOD FOR DETECTING HYDROCARBON DEPOSITS

CROSS-REFERENCE TO RELATED APPLICATIONS

The present application is a National Phase entry of PCT Application No. PCT/FR2014/052082, filed on Aug. 12, 2014, which is hereby fully incorporated herein by reference.

FIELD OF THE INVENTION

The invention relates to the field of offshore hydrocarbon deposits detection.

BACKGROUND OF THE INVENTION

The growing need for energy is inciting the development of novel means for detecting and locating geographic zones with a high hydrocarbon potential.

One of the techniques for detecting submarine petroleum deposits consists in monitoring the surface of a body of water in order to detect traces of natural hydrocarbon leaks therein. Indeed, a submarine deposit may communicate with fractures up to the sea bed thus allowing hydrocarbons to escape. These hydrocarbons having a lower density than that of water, they rise in a plume in the water column until a thin film of a few microns in thickness is formed on the water surface.

As 75% of the Earth is covered with water, the observation of surface traces of hydrocarbon leaks is typically based on images taken from aircraft or by satellites. In this regard, besides the use of optical imaging, Synthetic Aperture Radar (SAR) is generally used.

Medium-resolution (typically 25 m) radar sensors are commonly used to detect traces of hydrocarbon leaks. These images generally cover surface areas of 100 km by 100 km which may seem small for the exploration of oil traces at the scale of a sedimentary basin. In order to detect natural hydrocarbon leaks from petroleum systems (commonly referred to using the term "seep"), it is necessary to distinguish them, on one hand, from the other oil traces linked with pollution generated by humans (degassing of vessels and pollution from rigs commonly referred to using the term "spill") and, on the other hand, look-alike images (e.g. algal blooms) which may have the same signature as seeps on SAR images.

The current use of SAR images to identify traces of hydrocarbon leaks thus provides information with a reduced reliability which is merely qualitative, classifying detected hydrocarbon indices on a confidence scale.

Consequently, there is a need for an improvement of the detection techniques based on monitoring bodies of water in order to increase their reliability and be able to better detect submarine hydrocarbon deposits.

SUMMARY OF THE INVENTION

In order to address the problems described above, the present invention proposes a method for detecting and locating hydrocarbon deposits under a body of water. This method comprises:
acquiring images of a surface of the body of water taken at different times;
for each image:
identifying traces of hydrocarbon leaks;
generating a detection map indicative of probabilities of the presence of a hydrocarbon source around the identified traces of hydrocarbon leaks, by processing the image at least based on a criterion of distance to the identified traces of hydrocarbon leaks;
combining the detection maps generated to produce a hydrocarbon leak source location map.

As such, the method is based on cross-referencing of information from various images of the same body of water taken at different times. The use of images taken at different times particularly makes it possible to eliminate most transient traces of hydrocarbon leaks of human origin.

The method is based on a statistical approach based on identifying the surface traces of hydrocarbon leaks on each SAR image to generate a detection map, then combining the detection maps to produce a location map of the geographic zones liable to contain a hydrocarbon deposit. Indeed, the drift of hydrocarbons between the emission point thereof on the sea bed and the traces thereof on the sea surface can misrepresent the location of the submarine sources of these hydrocarbons. The drift of the hydrocarbons can typically be subject to random fluctuations associated with marine currents. By cross-referencing, by combination, the detection maps generated on the basis of a plurality of images of the same body of water, the invention makes it possible to reduce the bias introduced by this drift and identify more precisely the probable location of the submarine source of a hydrocarbon leak of natural origin. The statistical approach thus increases the reliability of the hydrocarbon deposit location maps generated.

The invention also makes it possible to provide not only qualitative information on the probability of the presence of a hydrocarbon deposit, but also quantitative information by cross-referencing by combination the images of the same body of water. The "combination" may consist of an addition of probabilities estimated using detection maps. The most probable location of the submarine source revealing a hydrocarbon deposit then corresponds to the points where the sum is the highest.

Moreover, the implementation of the method for analyzing images such as SAR images of a body of water makes it possible to provide quick and low-cost information on the location of hydrocarbon leaks of natural origin.

According to one embodiment, the images can cover an area of at least 100 kilometers by 100 kilometers.

Such images described as wide-swath can be obtained at least cost and cover a large geographic zone. The use of wide-swath images can also simplify repeatedly obtaining images of the same body of water. In this way, the images provide statistically more reliable information on the probable location of deposits.

According to one embodiment, the hydrocarbon leak source location map can be produced by combining detection maps generated from at least 50 images of the body of water.

Using a number of images of the same body of water greater than 50, the statistical approach of the method according to the invention makes it possible to effectively rule out the majority of traces of hydrocarbon leaks of human origin. Indeed, it has been observed that surface hydrocarbon slicks are evaporated in intervals of a few hours to a few days. Traces from degassing of a vessel or any other isolated pollution are then unlikely to be located in the same geographic zone on a plurality of successive images taken at different times. Upon combining the detection maps, these traces of human origin are not major contributors to the sum used to produce the location map.

According to one embodiment, the images can have pixels representing an area greater than 25 meters by 25 meters.

Such images are described as "medium" or "low" resolution. By making do with such images, the method can be implemented without having to take specific images. The method can indeed use pre-existing image banks acquired by observation satellites, such as ENVISAT and ERS. The geographic zone covered can thus be extended significantly with respect to existing detection techniques.

Moreover, using images having a "low" resolution, the same geographic zone can be covered by involving a smaller volume of data than images having pixels representing smaller areas. This reduction of the data volume makes it possible to implement the method more rapidly.

Furthermore, a greater number of images on the same body of water can then be taken into account without a perceptible negative impact on the speed of the method.

According to one embodiment, the images can be taken at time intervals between one day and several months.

The temporal resolution of the image acquisition can represent an effective means for sampling the frequency of appearance of traces of hydrocarbon leaks and as such distinguish between hydrocarbon indices of natural origin and those of human origin and look-alike images.

By obtaining images distributed over time over a period of several days or several months, typically 2, 5 or 10 months, it is possible to see whether the traces of hydrocarbon leaks are repeated over time. A trace of human origin typically appears in isolation even though it can be repeated along navigation routes or in the vicinity of oil rigs. The phenomenon of hydrocarbon leakage from natural deposits is assumed to be irregular over time but over long periods. Temporal image sampling over a long period thus makes it possible to distinguish natural hydrocarbon indices, where the repeatability thereof should be significant, from hydrocarbon indices of human origin such as pollution from boats where repeatability should theoretically remain low.

According to one embodiment, the images can be acquired using a device sensitive to wavelengths included in the visible and infrared range.

In the visible and infrared range, traces of hydrocarbon leaks appear in the form of specks contrasting with the ordinary color of a body of water. The detection of these traces in this range can be performed regardless of the wind strength. The wavelengths of the visible and infrared range are typically between 400 nm and 1 cm.

According to a further embodiment, the images can be acquired using a device sensitive to wavelengths included in the radar range.

The use of an apparatus sensitive in the radar range offers a greater contrast than the devices sensitive to wavelengths included in the visible and infrared range. Radar waves also allow observation at night and through bodies of cloud. The wavelengths of the radar range are typically between 1 cm and 1 m.

Advantageously, the method can further comprise, for each image:
  filtering traces of hydrocarbon leaks identified by morphological analysis to exclude traces of hydrocarbon leaks of human origin and look-alike images.

By ruling out the traces of hydrocarbon leaks of which the origin is clearly human, it is possible to render the hydrocarbon leak location map generated more reliable. It has been observed that the traces of hydrocarbon leaks of human origin are typically rectilinear or have a regular curve. This is particularly the case of traces originating from pollution by vessels. The traces outline a more complex pattern on the surface when they are of natural origin due to the marine currents causing the drift of the hydrocarbons rising to the surface. It is also possible to rule out the traces of hydrocarbon leaks corresponding to look-alike images, i.e. surface traces which merely have the appearance of a trace of hydrocarbon leaks, such as for example algal blooms.

According to one embodiment, the identification of traces of hydrocarbon leaks in an image can comprise searching for traces at locations where a wind of a speed generally between 3 meters per second and 10 meters per second is blowing.

The identification of traces of hydrocarbon leaks on SAR images may prove to be unreliable in the absence of any wind or when the wind exceeds a value of approximately 10 meters per second. Indeed, in the absence of any wind, the surface of a body of water does not generally comprise any chop. As such, the hydrocarbon slick and the surface of the surrounding water both form smooth surfaces reflecting radar waves similar to a plane mirror. It is then difficult to distinguish the trace of the hydrocarbon leak from the water on an SAR image when the wind is absent. In the presence of a strong wind having a speed greater than 10 meters per second, the surface of a body of water is subject to a significant chop. Similarly, the chop affects the hydrocarbon slick on the water surface. The reflection of the radar wave is then diffuse for these two entities which thus cannot be readily distinguished on the SAR image. On the other hand, in the presence of winds having an intermediate speed between 3 meters per second and 10 meters per second, the seawater is subject to chop whereas the hydrocarbon slick retains a smooth surface reflecting the radar waves similar to a plane mirror. Traces of hydrocarbon leaks are then readily identifiable due to a strong contrast with respect to the rest of the water on a SAR image.

According to one embodiment, images of a plurality of geographic zones can be acquired to generate respective detection maps, the combination of the detection maps generated for one of the geographic zones comprising a normalization on the basis of the number of images acquired for said geographic zone.

Such a normalization step makes it possible to increase the reliability of the location maps. The higher the number of images of a body of water, the more the cumulative data contained in these images offer statistically reliable information. It can thus be advantageous to assign a greater coefficient of reliability to the maps generated from a high number of images. A body of water for which only a small number of images are available, typically less than 10 images, can provide misleading information as it is statistically unreliable. Normalization makes it possible to correct such bias and only assign high presence probabilities to the geographic zones covered using a sufficient number of images.

According to one embodiment, the processing of each image on the basis at least of a criterion of distance to the identified hydrocarbon traces can comprise assigning to each point i of the image a value computed on the basis of the distance of the point i to the trace of the identified hydrocarbon leak closest to the point i.

The distance of a point to a hydrocarbon leak trace is a simple means to define a probability of the presence of a hydrocarbon source. More particularly, by measuring the distance of a point i to the trace of the closest hydrocarbon leak, a distance map can be generated. These distances can be associated with a function, for example a function that decreases when the position of the point i is moved away from a trace, to define probabilities of the presence of a deposit on the detection map.

More particularly, the value assigned to a point i of the image can be proportional to $\exp[-d_i^2/(2\sigma^2)]$, where $d_i$ denotes the distance of the point i to the trace of the closest hydrocarbon leak, and $\sigma^2$ represents a representative variance of a zone of influence of the trace of the hydrocarbon leak.

The adjustable parameter $\sigma$ of the probability function defining the value assigned to a point i of the image makes it possible to account for the influence of marine currents and other environmental parameters liable to influence the drift of a hydrocarbon leak. For example, the parameter $\sigma^2$ can be set as equal to 7.5 kilometers, which makes it possible to account effectively for the majority of current-related drifts while taking into consideration non-extensive areas to locate hydrocarbon deposits.

According to one specific embodiment, the combination of the detection maps generated can comprise, for each point i, the addition of the values assigned to the point i on each detection map.

This addition of the values assigned to each point on the detection maps produces new values representative of the repeatability of a trace over time. The sum obtained thus has a low value when the traces only appear in isolation and a high value when the traces appear regularly. This dependency with the repeatability naturally rules out the contribution to the probability of the presence of "spills" and increases the visibility of the locations of potential deposits.

Moreover, when the position of "seeps" is subject to fluctuations over time, the addition makes it possible to reduce the influence on the probability of presence displayed on a location map of the high-drift traces of the potential deposit. In this way, the addition of the values assigned to each point provides enhanced location information in respect of potential deposits.

BRIEF DESCRIPTION OF THE FIGURES

The method according to the invention will be understood more clearly on reading the following description of embodiments given by way of illustration, which are in no way limiting, and on observing the drawings hereinafter wherein.

For clarity reasons, the dimensions of the various elements represented in these figures are not necessarily in proportion with the actual dimensions thereof. In the figures, identical references correspond to identical elements.

DETAILED DESCRIPTION OF THE FIGURES

The invention relates to a method for analyzing images of the surface of a body of water suitable for detecting traces of hydrocarbon leaks of natural origin. This method also makes it possible to locate the most probable position of the source of these hydrocarbon leaks. The invention is based on a statistical approach suitable for distinguishing automatically, quickly and at a low cost the traces of hydrocarbon leaks of natural origin ("seeps") from those of human origin ("spills").

Figure 1:
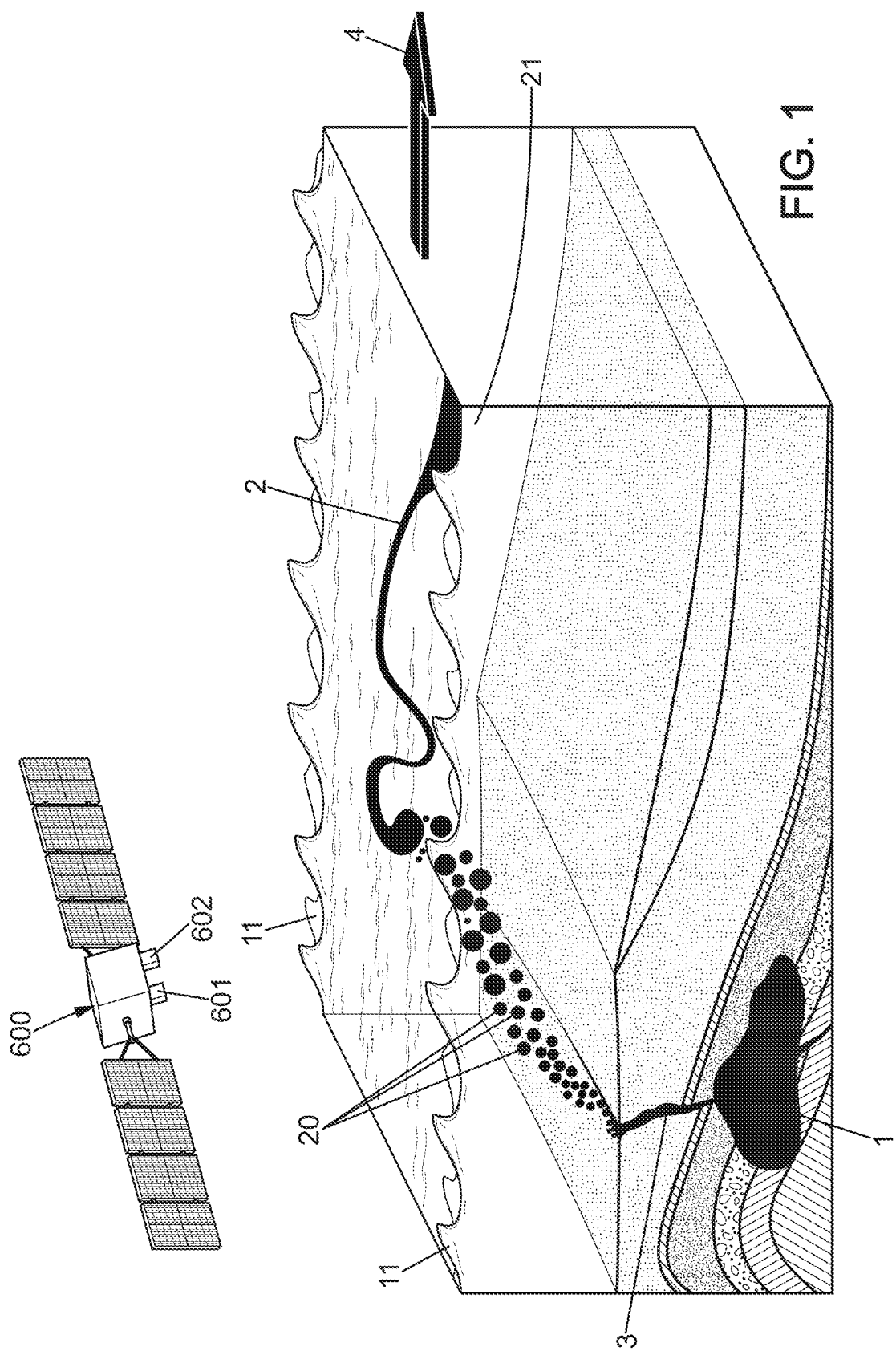
FIG. 1 is a schematic sectional perspective representation of a body of water, including a submarine deposit having a hydrocarbon leak leaving on the surface of the body of water a trace of hydrocarbon leak.

Submarine hydrocarbon deposits 1 can generally release a low quantity of hydrocarbons via fractures 3 in the sea bed. FIG. 1 illustrates schematically on a sectional perspective view a hydrocarbon leak 20 via such a fracture 3 from a deposit 1. The density of hydrocarbons, such as petroleum, is frequently less than that of water, and particularly seawater. For this reason, the hydrocarbons 20 rise from the fracture 3 to the surface 11, in order to form traces 2 of hydrocarbon leaks thereon.

These traces 2 of hydrocarbon leaks generally have a rippled profile with meanders, due to the random drift, according to the marine currents 4, of the hydrocarbons 20 rising to the surface 11.

On the surface, the traces 2 of hydrocarbon leaks form slicks 21 which remain smooth while the wind does not exceed a speed of the order of 10 meters per second.

The method according to the invention uses a bank of images of the surface of a body of water in order to identify "seeps" therein. This method then detects the hydrocarbon leaks of natural origin and locates the most probable release point thereof.

The images of a body of water can be obtained by means of aircraft flyovers, or by accessing the images taken by observation satellites 600, such as ENVISAT or ERS. These apparatuses are or can be equipped with optical sensors 601 and/or radar sensors 602.

The choice of the size of the images, the resolution and the number thereof for the same body of water are adjustable parameters of the invention.

The synthetic aperture radar (SAR) images routinely used for identifying traces of hydrocarbon leaks have a so-called medium resolution. A medium resolution corresponds herein to pixels on the image representing an area of approximately 25 m by 25 m, i.e. an ability to detect objects having a size of more than 25 m. These sensors can cover an area of 100 km by 100 km with this resolution.

The method according to the present invention can function with images having low nominal resolutions, i.e. having pixels representing an area of 150 m by 150 m, and covering on an image an area of 400 km by 400 km. As such, the geographic zone studied is enlarged thereby and the quantity of information to be processed per image reduced. Indeed, it has been observed that seeps 2 generally extend over several kilometers in length and several hundred meters in width, which renders them detectable on low-resolution images as described above.

Moreover, the number of images available with this resolution is great and they cover a greater surface area. Indeed, observation satellites have accumulated such time-stamped images with over 50 images for the same geographic zone on a part of the seas and oceans in the vicinity of the coasts. The invention can thus be implemented without needing to set up costly observation means to compile image banks.

It is advantageous to have a high number, preferably greater than 50, of images of the same body of water taken at different times. The "seeps" 2 are reproduced in a random and repeated fashion. The "spills" 201, 202 occur in a more isolated fashion due for example to pollution created by humans.

As such, with a number greater than 50 of images taken at different times of the same body of water, it is possible to distinguish between "seeps" and "spills", using the frequency of occurrence of traces of hydrocarbon leaks.

Figure 2:
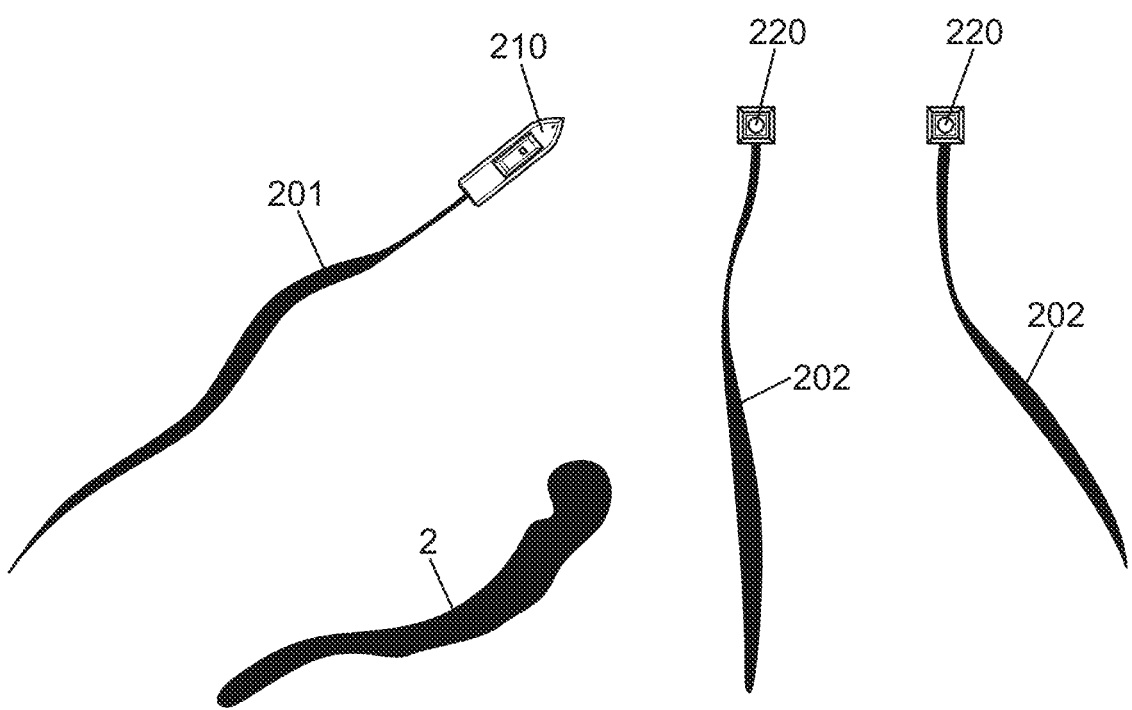
FIG. 2 is a schematic top view representation of various traces of hydrocarbons of natural origin and of pollution on a body of water.

FIG. 2 illustrates schematically several examples of traces 2, 201, 202 of hydrocarbon leaks which can typically appear on an image. Only the trace 2 has a natural origin. It is distinguished from the others by the ripples thereof and the irregular shape thereof. The trace 201 is rectilinear and follows the wake of a vessel 210, which can be identifiable on an image. In the absence of a vessel on the image, the presence of a trace of similar shape to the trace 201 can be attributed to a human origin if it is situated on a known navigation route. The traces 202 are also longilineal, rectilinear or curved, and are linked with pollution from a rig 220. The rigs 202, which are fixed elements, can be identifiable on the images.

An optional step for preliminary discrimination of the traces 201, 202 of hydrocarbon leaks the origin whereof is clearly artificial can be implemented. This selection can be performed on shape criteria or by cross-referencing the traces 201, 202 with the position of known rigs or navigation routes. This filtering based on morphological analysis reduces the quantity of data to be taken into account when implementing the subsequent steps of the method.

However, some traces can have the appearance of a "seep" without being from a hydrocarbon deposit. This can, for example, arise in the presence of strong surface currents distorting the traces left by vessels or in the presence of rain cells, oceanic fronts or algal blooms. In order to distinguish these traces from "seeps", the invention uses the temporal resolution (repeatability) of the SAR data acquired for the same body of water.

It is then advantageous to have SAR images of the same body of water taken over a long period spread over several months or several years. Such an observation period makes it possible to reduce the location bias linked with particular weather conditions or seasonal effects on marine currents causing drifts. It is also advantageous to have images taken at relatively close time intervals. Time intervals spread over periods between one day and a few months for the imaging make it possible to achieve a satisfactory acquisition frequency/acquisition period ratio.

Figure 3A:
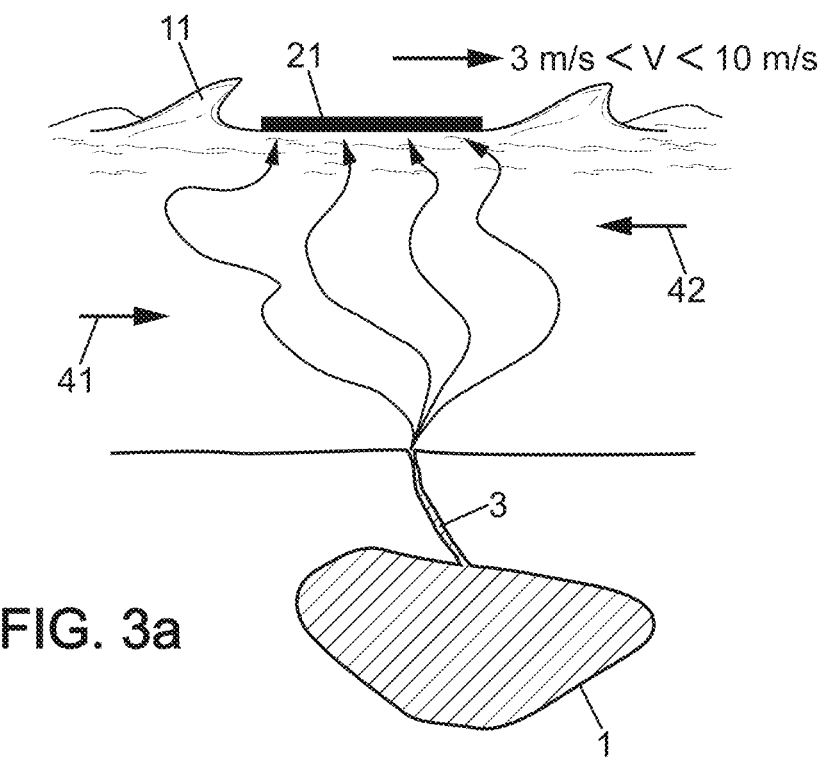
FIG. 3a is a schematic side view representation of a body of water comprising hydrocarbon leaks escaping via a fault of a submarine deposit, and a hydrocarbon slick on the surface.

The method according to the invention identifies on each image acquired the traces 2 of hydrocarbon leaks. The identification is performed either on images acquired with an optical sensor 601 sensitive to wavelengths included in the range encompassing the visible and infrared range, or on images acquired with a radar sensor 602. The images acquired with an "optical" sensor make it possible to identify hydrocarbon slicks 21 regardless of the wind speed, but at daytime and during clear weather. The images acquired with a "radar" sensor make it possible to view hydrocarbon slicks 21 both at daytime and at night, and through bodies of cloud, but in the presence of particular wind conditions, as represented schematically in FIGS. 3a to 3c. FIG. 3a represents a body of water swept on the surface by a wind having a speed between 3 meters per second and 10 meters per second. In such a configuration, the hydrocarbon slick 21 remains smooth whereas the surrounding water is disturbed by surface chop. On a radar image, this scenario makes it possible to view with a strong contrast the slick 21 which reflects the waves similar to a mirror. As the distorted surface of the surrounding water does not act as a mirror, it is perceived with a different color on the radar image.

Figure 3B:
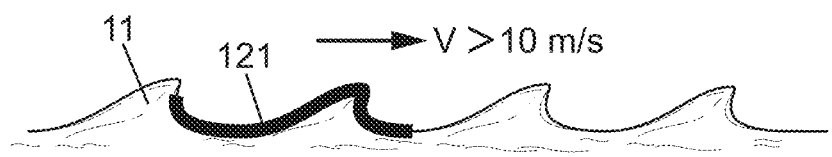
FIGS. 3b and 3c are schematic side view representations of a hydrocarbon slick on the surface of a body of water subject to different wind speeds.
Figure 3C:

FIG. 3b represents a body of water swept on the surface by a wind having a speed greater than 10 meters per second. The hydrocarbon slick 121 affected by the chop has a rough surface similar to that of the surface 11 of the surrounding water. The slick 121 and the surface 11 of the water will then typically have the same color on the radar image.

FIG. 3b represents a body of water swept on the surface by a wind having a speed less than 3 meters per second. The slick 21 remains smooth like the surface 110 of the surrounding water. In this scenario, the radar image represents the slick 21 and the surface 110 of the water with the same color, and it is not possible to distinguish between these two entities on a radar image. However, an optical image would make it possible to perceive a slick 21 in a different color even in the presence of such a weak wind.

It thus seems that the best observation conditions arise when the wind sweeping a body of water has a speed between 3 meters per second and 10 meters per second. This configuration is equally suitable for optical or radar imaging. Consequently, the images acquired can also indicate the field of the wind sweeping the geographic zone represented on an image. In practice, this wind field can be extracted from an image using known tools.

After having identified the traces 2 of hydrocarbon leaks on the images acquired, the method proposes, for each image, generating a detection map showing, around each trace 2 of hydrocarbon leaks, the probable location of the submarine source of the hydrocarbon leaks.

As represented in FIGS. 1 and 3a, the hydrocarbons 20 escape via a fracture 3 of a deposit rising to the surface while being subject to marine currents 4, 41, 42. These currents can be the cause of a significant drift of the traces 2 of hydrocarbon leaks, which are thus not found to be directly above the deposits 1 producing same.

The method generates a map for detecting the probable location of the source of each trace 2 of hydrocarbon leaks at least based on a criterion of distance of a point of the surface to the identified traces 2.

An embodiment represented in FIG. 4A consists in generating a distance map wherein each point 7, i of an image is indicated by a color which is based on the distance 6, $d_i$ thereof to the closest trace 2 of hydrocarbon leaks.

Figure 4:
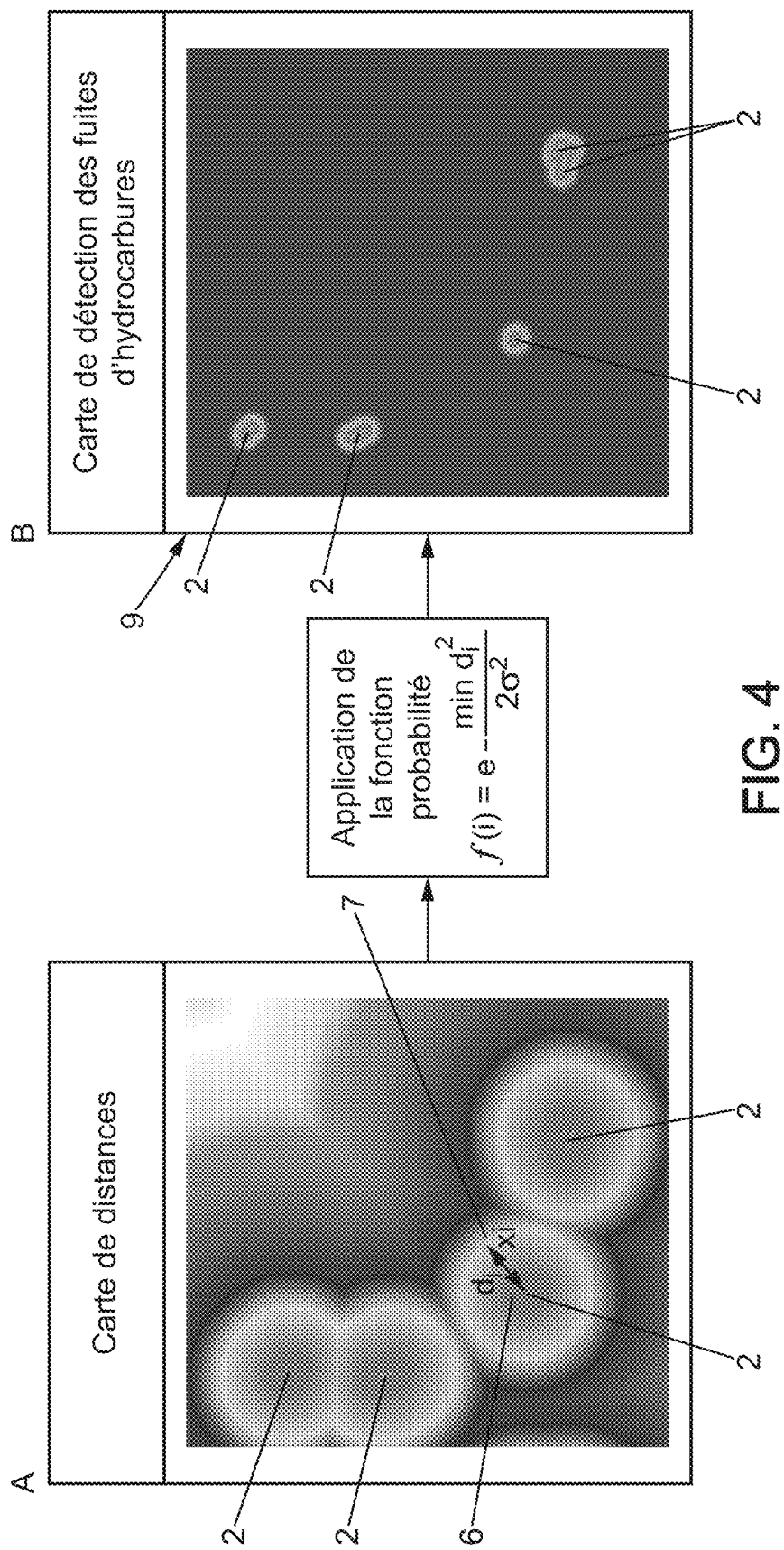
FIG. 4 is a schematic representation: A of a map of distances of the points of an image to the traces of hydrocarbon leaks of that image, and B of a hydrocarbon leak detection map obtained by applying a probability function to the distance map A.

An embodiment represented in FIG. 4 element A consists in generating a distance map wherein each point 7, i of an image is indicated by a color which is based on the distance 6, $d_i$ thereof to the closest trace 2 of hydrocarbon leaks.

Based on the knowledge available on the imaged geographic zone, it is then possible to generate a detection map 9 as represented in FIG. 4 element B by applying to each point i of the image in FIG. 4 element A a probability function.

By way of example, a Gaussian function such as the function f defined for any point i by the expression $f(i)=\exp[-\min d_i^2/(2\sigma^2)]$ can be used. In this expression, $d_i$ denotes the distance 6 of the point 7, i to the trace 2 closest to this point, and $\sigma^2$ represents a variance, defining a zone of influence of the trace of the hydrocarbon leak. A typical zone of influence can be equal to 8 km, the value of $\sigma^2$ being capable, in this example, of being set to 7.5 km. The parameter a is an adjustment variable which can be modified if suggested by the conditions of the geographic zone represented in the image. Moreover, in the event of a current of known vector being present, it is possible to apply any other probability function accounting for these additional data.

The detection maps 9 obtained in this way form a data set suitable for use for cross-referencing making it possible by combination to converge towards a most probable and reliable position of the source point from which the trace 2 of hydrocarbon leaks originates. The "combination" can consist of an addition of the probabilities displayed on the detection maps 9.

By way of example, the addition of the probabilities can be performed point by point based on each detection map generated for the same body of water.

The combination step makes it possible to generate a grid of probabilities of occurrence of a hydrocarbon trace corresponding to the temporal resolution of the leak phenomenon over time. For each point 7, i the probability of the presence of a deposit on each detection map is taken into account with a view to obtaining by addition a value integrating the variations of this probability over time. In this way, the traces 2 of hydrocarbon leaks of human origin contribute less to the probability of the presence of a deposit than the traces 2 of hydrocarbon leaks of natural origin, which are frequently found on successive images as mentioned above.

The location map generated based on this combination is comparable to an overlay image, also referred to as a "stack" image.

The statistical approach of the method according to the invention involves the use of a high number, preferably greater than 50, of images of the same body of water. In order to differentiate the location maps based on the number of detection images available for the generation thereof, a normalization step can be implemented.

Figure 5A:
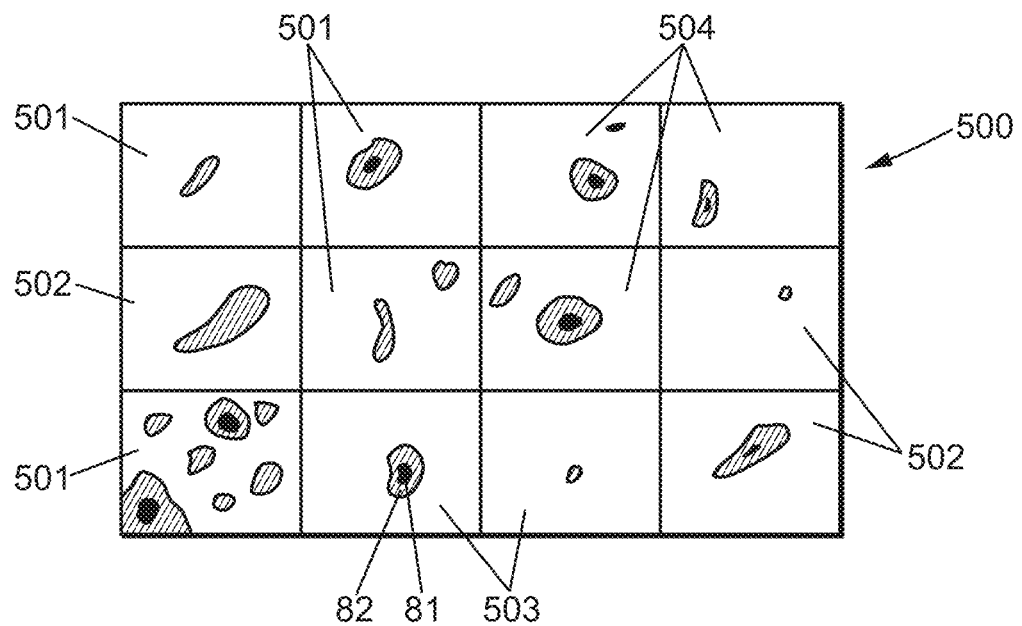
FIGS. 5a and 5b are schematic representations of hydrocarbon leak location maps before normalization and after normalization, respectively.
Figure 5B:
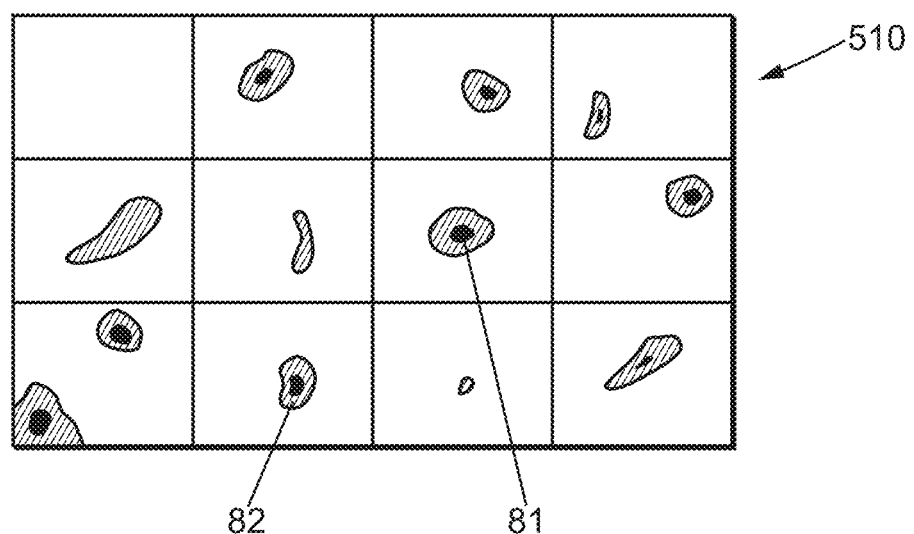

FIGS. 5a and 5b represent a location map obtained before normalization and after normalization respectively.

FIG. 5a represents a location map 500 comprising twelve different geographic zones. In each zone, solid 81 or hatched 82 shapes represent probable locations of hydrocarbon deposits. The solid shapes 81 are those for which the probability of the presence of a deposit was computed as being the highest.

Each geographic zone was mapped using a different number of images. The geographic zones 501 were obtained with less than ten images, the geographic zones 502, with more than ten but less than thirty images, the geographic zones 503 with more than thirty but less than fifty images and the geographic zones 504 with more than fifty images. The location map of the FIG. 5a indicates evidently that the geographic zones 501 comprise sites having a high probability of the presence of hydrocarbon deposits.

FIG. 5b represents a location map 510 obtained after normalization of the location map 500. Normalization consists in correcting the values assigned to the points of a location map representing a geographic zone by a coefficient based on the number of images used to generate the location map in this geographic zone.

It can be seen in FIG. 5b that the sites considered to be potentially rich in hydrocarbons in the geographic zones 501 according to FIG. 5a prove to be less promising sites for a hydrocarbon deposit after normalization. As such, normalization on makes it possible to correct bias linked with an insufficient number of data.

The invention described above makes it possible to obtain a map of the probable locations of hydrocarbon deposits by providing quantitative and not merely qualitative information. The method implemented does not require the use of costly resources and can be implemented rapidly. The statistic approach of the method makes it possible to reduce on the location maps the contribution to the values of the probability of the presence of hydrocarbon deposits of traces of hydrocarbon leaks of human origin.

When a location map has been obtained based on low-resolution SAR data, it is possible to supplement the analysis of images of a body of water using images offering superior resolution, in order to reduce the extent of the area taken into consideration for the probable location of a deposit. Moreover, once a reliable location map has been generated, it is possible to overlay this map with a corresponding map of the bottom of the body of water, in order to identify more accurately the probable origin of the hydrocarbon leak based on the bathymetry of the environment.

The invention is not restricted to the embodiments described above. In particular, the method according to the invention can be implemented with images having superior resolutions and/or covering smaller areas.

The invention claimed is:

1. A method for detecting and locating a hydrocarbon deposit under a body of water, the method comprising:
   acquiring images of a surface of the body of water taken at different times;
   for each image:
      identifying traces of hydrocarbon leaks in the image;
      generating a detection map indicative of probabilities of the presence of a hydrocarbon source around the identified traces of hydrocarbon leaks, by processing the image at least based on a criterion of distance to the identified traces of hydrocarbon leaks;
      combining the detection maps generated to produce a hydrocarbon deposit leak source location map, and
      wherein the processing of each image on the basis at least of a criterion of distance to the identified hydrocarbon traces comprises assigning to each point i of the image a value computed on the basis of the distance of the point i to the trace of the identified hydrocarbon leak closest to the point i, and the value assigned to a point i of the image is proportional to $\exp[-\min d_i^2/(2\sigma^2)]$, where $\min d_i^2$ denotes a minimum distance squared of the point i to a trace of a closest hydrocarbon leak, and $\sigma^2$ represents a representative variance of a zone of influence of the trace of the hydrocarbon leak.

2. The method of claim 1, wherein the images cover an area of at least 100 km by 100 km.

3. The method according to claim 1, wherein the hydrocarbon leak source location map is produced by combining detection maps generated from at least 50 images of the body of water.

4. The method according to claim 1, wherein the images have a pixel representing an area greater than 25 metres by 25 metres.

5. The method according to claim 1, wherein the images are taken at time intervals between one day and several months.

6. The method according to claim 1, wherein the images are acquired using a device sensitive to wavelengths included in the visible and infrared range.

7. The method according to claim 1, wherein the images are acquired using a device sensitive to wavelengths included in the radar range.

8. The method according to claim 1, further comprising, for each image:

filtering traces of hydrocarbon leaks identified by morphological analysis to exclude traces of hydrocarbon leaks of human origin and look-alike images.

9. The method according to claim 1, wherein images of a plurality of geographic zones are acquired to generate respective detection maps, the combination of the detection maps generated for one of the plurality of geographic zones comprising a normalisation on the basis of a number of images acquired for said geographic zone.

10. The method according to claim 1, wherein the combination of the detection maps generated comprises, for each point i, addition of the values assigned to the point i on each detection map.

* * * * *

UNITED STATES PATENT AND TRADEMARK OFFICE
CERTIFICATE OF CORRECTION

PATENT NO. : 10,895,665 B2
APPLICATION NO. : 15/503339
DATED : January 19, 2021
INVENTOR(S) : Dhont et al.

It is certified that error appears in the above-identified patent and that said Letters Patent is hereby corrected as shown below:

In the Claims

Column 10, Line 48:
Delete "method of" and insert -- method according to --, therefor.

Signed and Sealed this
Thirtieth Day of March, 2021

Drew Hirshfeld
*Performing the Functions and Duties of the
Under Secretary of Commerce for Intellectual Property and
Director of the United States Patent and Trademark Office*